United States Patent
Sriram et al.

(10) Patent No.: US 9,583,458 B2
(45) Date of Patent: Feb. 28, 2017

(54) METHODS FOR BONDING A HERMETIC MODULE TO AN ELECTRODE ARRAY

(71) Applicant: The Charles Stark Draper Laboratory, Inc., Cambridge, MA (US)

(72) Inventors: Tirunelveli Sriram, Acton, MA (US); Brian Smith, Cambridge, MA (US); Bryan Mclaughlin, Cambridge, MA (US); John Lachapelle, Princeton, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 860 days.

(21) Appl. No.: 13/836,582

(22) Filed: Mar. 15, 2013

(65) Prior Publication Data
US 2014/0273345 A1  Sep. 18, 2014

(51) Int. Cl.
*H01K 3/10* (2006.01)
*H01L 23/00* (2006.01)
(Continued)

(52) U.S. Cl.
CPC .............. *H01L 24/83* (2013.01); *A61B 5/0031* (2013.01); *A61B 5/04001* (2013.01); *A61N 1/05* (2013.01);
(Continued)

(58) Field of Classification Search
CPC .......... H01L 24/83; H01L 24/85; H01L 23/13; H01L 23/147; H01L 23/3107; H01L 2924/12042; H01L 24/45; H01L 2924/00014; H01L 23/4985; H01L 25/0657; H01L 2924/0002; H01L 2924/07802;H01L 2224/85; H01L 2224/45169; H01L 2924/00; H01L 2924/0001; H01L 2224/00014; H01L 2224/05599; A61N 1/375; A61N 1/05; A61N 1/0543; A61B 5/0031; A61B 5/04001; Y10T 29/49128; Y10T 29/49165
(Continued)

(56) References Cited

U.S. PATENT DOCUMENTS 4,915,981 A * 4/1990 Traskos ............... H05K 3/0032
216/65
5,174,242 A   12/1992 Takeuchi
(Continued)

OTHER PUBLICATIONS

International Search Report and Written Opinion dated Jul. 14, 2014 in connection with PCT/US2014/025079.

*Primary Examiner* — Donghai D Nguyen
(74) *Attorney, Agent, or Firm* — Nutter McClennen & Fish LLP; John J. Penny, V.; Ashley T. Brzezinski

(57) ABSTRACT

A method for bonding a hermetic module to an electrode array including the steps of: providing the electrode array having a flexible substrate with a top surface and a bottom surface and including a plurality of pads in the top surface of the substrate; attaching the hermetic module to the bottom surface of the electrode array, the hermetic module having a plurality of bond-pads wherein each bond-pad is adjacent to the bottom surface of the electrode array and aligns with a respective pad; drill holes through each pad to the corresponding bond-pad; filling each hole with biocompatible conductive ink; forming a rivet on the biocompatible conductive ink over each pad; and overmolding the electrode array with a moisture barrier material.

6 Claims, 7 Drawing Sheets

(51) Int. Cl.
*A61N 1/375* (2006.01)
*A61B 5/00* (2006.01)
*H01L 23/13* (2006.01)
*H01L 23/14* (2006.01)
*H01L 23/31* (2006.01)
*A61B 5/04* (2006.01)
*A61N 1/05* (2006.01)
*H01L 25/065* (2006.01)
*H01L 23/498* (2006.01)

(52) U.S. Cl.
CPC ............... *A61N 1/375* (2013.01); *H01L 23/13* (2013.01); *H01L 23/147* (2013.01); *H01L 23/3107* (2013.01); *H01L 24/85* (2013.01); *A61N 1/0543* (2013.01); *H01L 23/4985* (2013.01); *H01L 24/45* (2013.01); *H01L 25/0657* (2013.01); *H01L 2224/45169* (2013.01); *H01L 2224/85* (2013.01); *H01L 2924/0002* (2013.01); *H01L 2924/00014* (2013.01); *H01L 2924/07802* (2013.01); *H01L 2924/12042* (2013.01)

(58) Field of Classification Search
USPC ...... 29/831, 846, 852; 216/65; 118/314, 315
See application file for complete search history.

(56) References Cited

U.S. PATENT DOCUMENTS

| | | | |
|---|---|---|---|
| 6,958,095 B2 * | 10/2005 | Kakimoto | H01L 21/67092 |
| | | | 118/314 |
| 7,257,446 B2 | 8/2007 | Greenberg et al. | |
| 7,323,142 B2 | 1/2008 | Pendo et al. | |
| 7,323,634 B2 | 1/2008 | Speakman | |
| 7,480,988 B2 | 1/2009 | Ok et al. | |
| 7,623,335 B2 | 11/2009 | Stevenson et al. | |
| 7,813,796 B2 | 10/2010 | Greenberg et al. | |
| 8,000,804 B1 | 8/2011 | Wessendorf et al. | |
| 8,285,380 B2 | 10/2012 | Greenberg et al. | |
| 2010/0121438 A1 | 5/2010 | Jarvik | |
| 2013/0329373 A1 | 12/2013 | Smith et al. | |

* cited by examiner

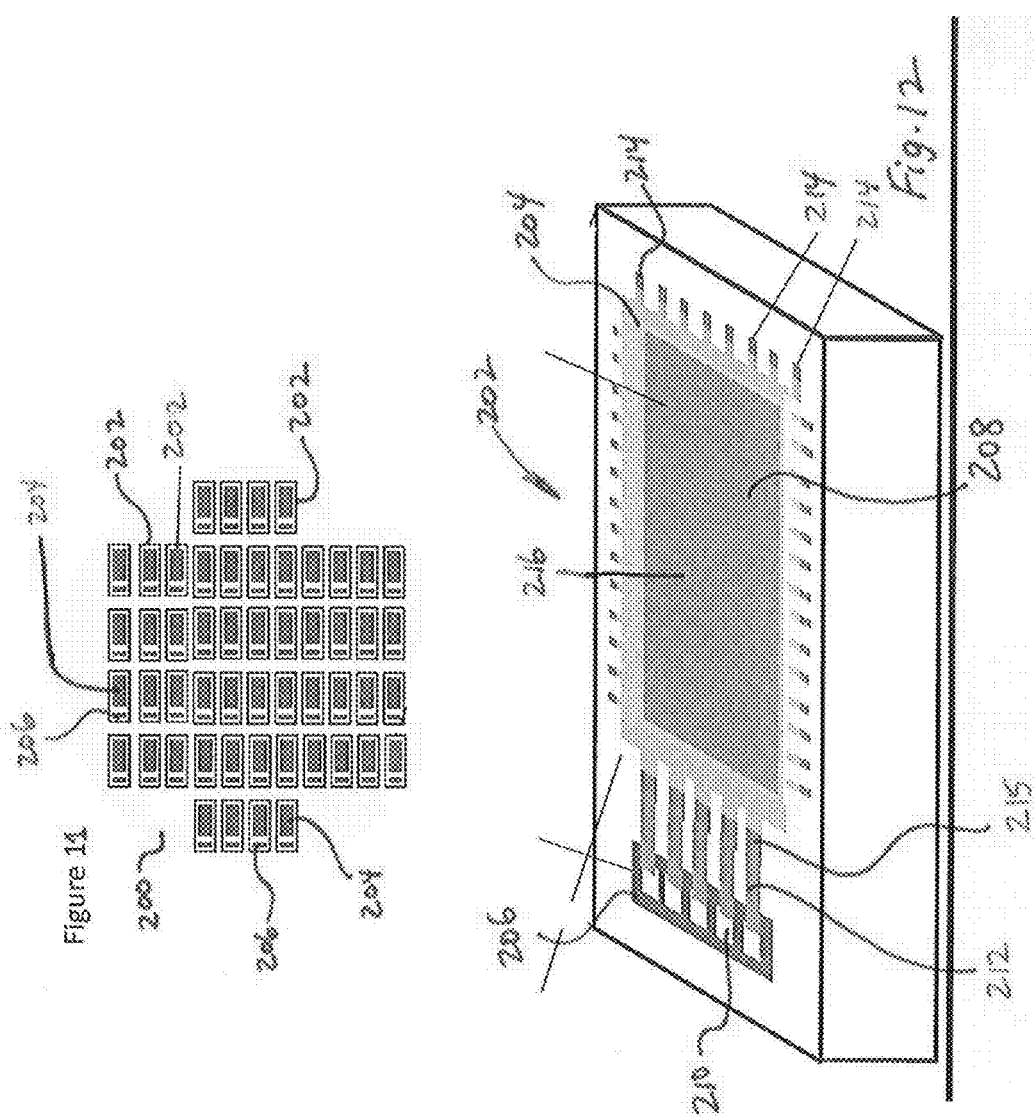

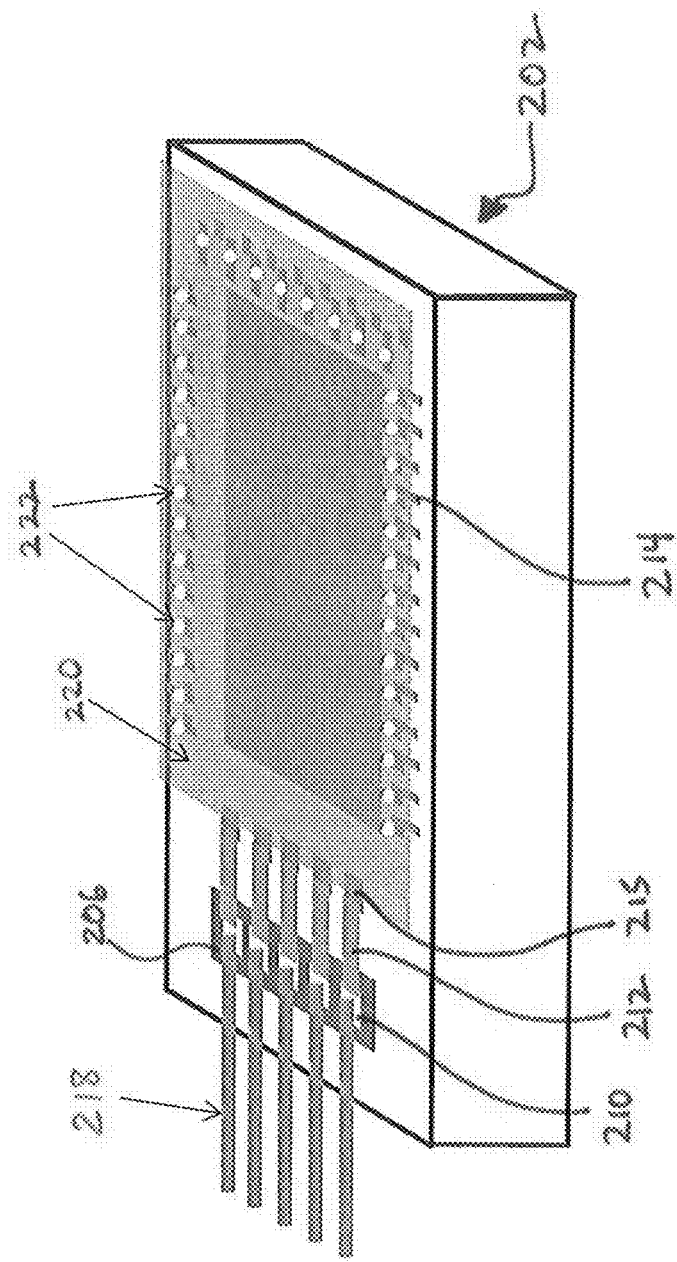

METHODS FOR BONDING A HERMETIC MODULE TO AN ELECTRODE ARRAY

BACKGROUND OF THE DISCLOSURE

1. Field of the Disclosure

The subject disclosure relates to systems and methods for interconnecting lead wires and bond pads, and more particularly to an improved biocompatible interconnection methods for attaching a hermetic implantable bond pad array to a miniature flexible-circuit electrode array and external lead wires.

2. Background of the Related Art

Various methods are used to interconnect hermetic modules, electrode arrays, and lead wires. Platinum wires co-fired with ceramic, laser welding, anisotropic conductive film, thermo-compression bonding, electro-deposition, and plating up Platinum to form rivets are some of the approaches. Often the connection is to a hermetic Titanium enclosure with electronics inside this hermetic volume.

Techniques for some examples are illustrated in U.S. Pat. No. 7,257,446 issued on Aug. 14, 2007 to Greenberg et al., U.S. Pat. No. 7,480,988 issued on Jan. 27, 2009 to Ok et al., U.S. Pat. No. 7,813,796 issued on Oct. 12, 2010 to Greenberg et al., U.S. Pat. No. 8,285,380 issued on Oct. 9, 2012 to Greenberg et al. and U.S. Ser. No. 13/490,189.

SUMMARY OF THE INVENTION

There are problems and drawbacks associated with the prior art approaches such as poor interconnect density. The best prior art rivet techniques achieve two connections per square millimeter. There is a need, therefore, for an improved method which permits increased connection density such as by an order of magnitude while insuring reliable and adequate connections.

In one embodiment, the subject technology interconnects a hermetic module bond-pad array (e.g., a medical implantable electronics module) to an electrode pad array and to external lead wires using micro-ink-jet or aerojet printing of bio-compatible conductive ink. In one embodiment, the ink contains Platinum. The method may use printed, bio-compatible mushroom vias and/or laser forming of vias to get via sizes below 50 microns, which allows a significant increase in connection density. The subject technology also includes a mechanically robust method of connecting to lead wires.

In another embodiment, the method for bonding a hermetic module to an electrode array includes the steps of: providing the electrode array having a flexible substrate with a top surface and a bottom surface and including a plurality of pads in the top surface of the substrate; attaching the hermetic module to the bottom surface of the electrode array, the hermetic module having a plurality of bond-pads wherein each bond-pad is adjacent to the bottom surface of the electrode array and aligns with a respective pad; drill holes through each pad to the corresponding bond-pad; filling each hole with biocompatible conductive ink; forming a rivet on the biocompatible conductive ink over each pad; and overmolding the electrode array with a moisture barrier material.

The pads may be annular. The hermetic module is attached to the electrode array with a bio-compatible insulating adhesive. Preferably, the drilling of the holes is done by a laser and the holes are substantially circular and less than 50 microns in diameter. The method may also include the step of using an inkjet process to fill each hole with the biocompatible conductive ink.

In still another method for attaching a lead wire to a module frame, wherein the module frame including at least one module pad, includes the steps of: drilling a hole in the hermetic module frame adjacent the at least one module pad; feeding an electrode wire through the hole; securing the wire in place within the hole; connecting the at least one module pad to the hole and thereby the wire; and overmolding the alumina module frame. The wire may be secured by wrapping back onto itself and welding. Connecting the at least one module pad to the hole and thereby the wire may be done by applying a printed conductive ink trace. The method can also include filling the hole with conductive epoxy, wherein the epoxy is applied in a mushroom topology using an ink-jet or aerojet printing process. The module frame preferably includes a plurality of module pads and a plurality of corresponding holes with a feedthrough density greater than 2/mm². The method may also include the steps of: forming another module assembly according to claim 7 and stacking the module assemblies; and providing a connective via between the two stacked modules.

A further method for bonding a hermetic module to an electrode array and attaching a lead wire thereto, wherein the electrode array including at least one module pad, includes the steps of: providing the electrode array having a substrate with a top surface and a bottom surface, wherein the at least one module pad is in the top surface of the substrate; attaching the hermetic module to the bottom surface of the electrode array, the hermetic module having at least one bond-pad, wherein the bond-pad is adjacent to the bottom surface of the electrode array and aligns with the at least one module pad; drilling a first hole through the at least one module pad to the at least one bond-pad; filling the first hole with biocompatible conductive ink; forming a rivet on the biocompatible conductive ink over the at least one module pad; drilling a second hole in the electrode array and hermetic module adjacent the at least one module pad; feeding an electrode wire through the second hole; securing the wire in place within the second hole; connecting the at least one module pad to the hole and thereby the wire; and overmolding the electrode array and hermetic module. The electrode array and hermetic module may combine to form a medically implantable electronics module.

It should be appreciated that the present technology can be implemented and utilized in numerous ways, including without limitation as a process, an apparatus, a system, a device, a method for applications now known and later developed. These and other unique features of the technology disclosed herein will become more readily apparent from the following description and the accompanying drawings.

BRIEF DESCRIPTION OF THE DRAWINGS

So that those having ordinary skill in the art to which the disclosed technology appertains will more readily understand how to make and use the same, reference may be had to the following drawings.

FIG. 11 is a top view of a substrate wafer with an array of modules in accordance with another embodiment of the subject technology.

FIG. 12 is a perspective view of a single module 202 after readiness for separation from the wafer is shown FIG. 13 is a perspective view of a single module post singulation processing to prepare for connection to an electrode array.

DETAILED DESCRIPTION OF PREFERRED EMBODIMENTS

Figure 1:
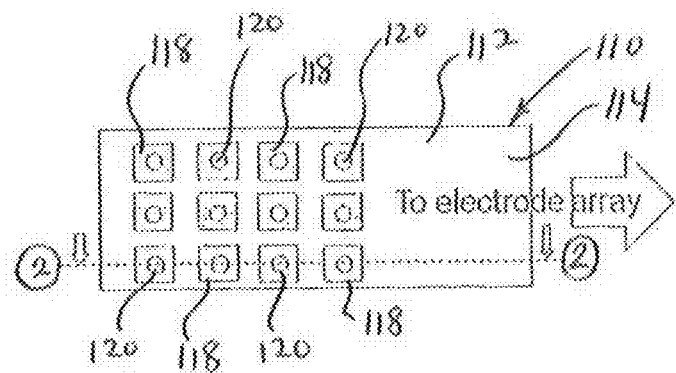
FIG. 1 is a top view of an electrode array in accordance with the subject technology.

The present disclosure overcomes many of the prior art problems associated with creating hermetic micropackages. The advantages, and other features of the systems and methods disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

All relative descriptions herein such as left, right, up, and down are with reference to the Figures, and not meant in a limiting sense. Unless otherwise specified, the illustrated embodiments can be understood as providing exemplary features of varying detail of certain embodiments, and therefore, unless otherwise specified, features, components, modules, elements, and/or aspects of the illustrations can be otherwise combined, interconnected, sequenced, separated, interchanged, positioned, and/or rearranged without materially departing from the disclosed systems or methods. Additionally, the shapes and sizes of components are also exemplary and unless otherwise specified, can be altered without materially affecting or limiting the disclosed technology.

Referring now to FIGS. 1-6, a series of figures depicting the steps for forming an electrode array and bonding a hermetic module to the electrode array to form a hermetic micropackage 100 in accordance with the subject technology is shown. The micropackage 100 is shown in cross-sectional view in FIG. 6.

Figure 2:
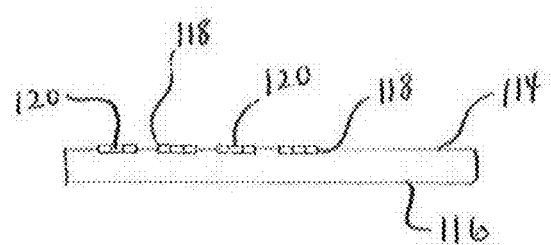
FIG. 2 is a cross-sectional view of the electrode array along line 2-2 of FIG. 1.

Referring now in particular to FIGS. 1 and 2, a top view and cross-sectional view along line 2-2 of an electrode array 110 in accordance with the subject technology is shown. The electrode array 110 includes a substrate 112 of a flexible circuit board such as KAPTON or PYRALUX materials available from DuPont or other desired polyimide laminates. The substrate 112 has a top surface 114 and an opposing bottom surface 116. The electrode array 110 also includes a plurality of pads 118 in the top surface 114 of the substrate 112. Each pad 118 is rectangular in shape with a central circular aperture 120. Not only is the number and arrangement of the pads variable but the size and shape is also variable depending upon the hermetic micropackage 100.

Figure 3:
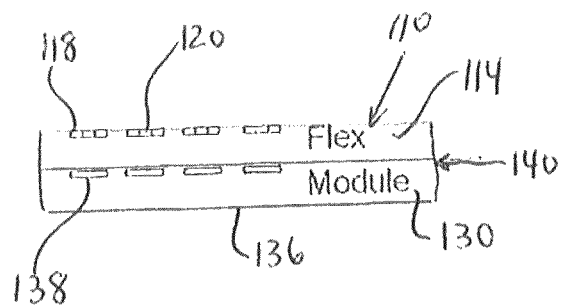
FIG. 3 is a cross-sectional view of the electrode array of FIG. 1 after attachment of a hermetic module in accordance with the subject technology.

Referring now to FIG. 3, a cross-sectional side view of the electrode array 110 is shown after attachment of a hermetic module 130 in accordance with the subject technology. The hermetic module 130 includes a substrate 132 with a top surface 134 and a bottom surface 136. A plurality of bond-pads 138 are embedded in the top surface 134. Preferably, the top surface 134 is substantially planar.

The top surface 134 of the hermetic module 130 is attached to the bottom surface 116 of the electrode array 110 so that each bond-pad 138 aligns directly below a respective pad 118. Various attachment methods now known and later developed may be used to couple the electrode array 110 and hermetic module 130 together. In one embodiment, the hermetic module 130 is attached to the electrode array 110 with a bio-compatible conductive adhesive 140.

Figure 4:
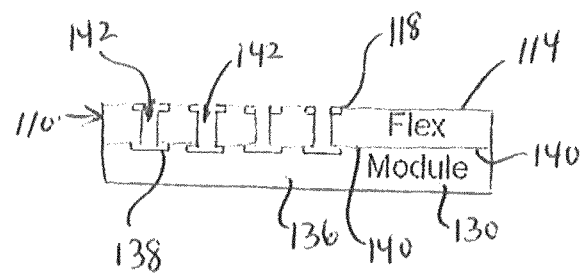
FIG. 4 is a cross-sectional view of the electrode array of FIG. 1 with drilled holes in accordance with the subject technology.

Referring now in particular to FIG. 4, another cross-sectional view of the electrode array 110 with holes 142 is shown. The holes 142 are formed to extend from each pad 118 of the electrode array 110 to the corresponding bond-pad 138 of the hermetic module 130. In one embodiment, the holes 142 are laser drilled.

Figure 5:
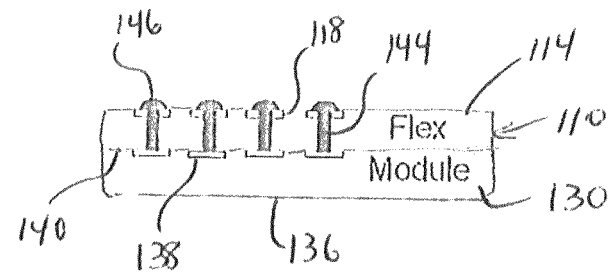
FIG. 5 is a cross-sectional view of the electrode array of FIG. 1 with ink filling the drilled holes in accordance with the subject technology.

Referring now in particular to FIG. 5, a cross-sectional view of the electrode array 110 with ink 144 filling the holes 142 is shown accordance with the subject technology. Each hole is preferably filled with biocompatible conductive ink 144 to form a connection from each pad 118 of the electrode array 110 to the corresponding bond-pad 138 of the hermetic module 130. In one embodiment, an inkjet printing process is used to fill the holes 142 with the ink 144. The inkjet printing process can also be used to form rivets 146 on the biocompatible conductive ink over each pad. The rivets 146 can be rounded to form a mushroom like top or other shape.

Figure 6:
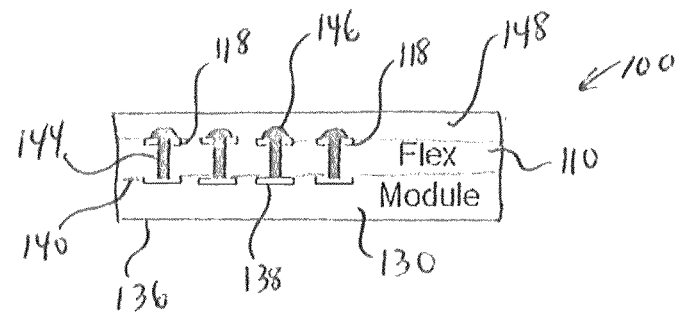
FIG. 6 is a cross-sectional view of the electrode array of FIG. 1 the electrode array overmolded to form a micropackage in accordance with the subject technology.

Referring now in particular to FIG. 6, a cross-sectional view of the electrode array 110 after having been overmolded to form the micropackage 100 is shown. The overmolding process creates a moisture barrier 148 for protecting the resulting assembly.

Figure 7:
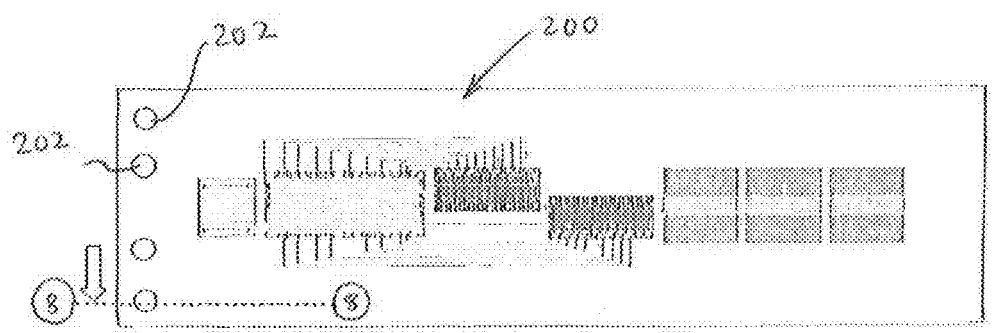
FIG. 7 is a top view of an alumina module frame in accordance with the subject technology.
Figure 8:
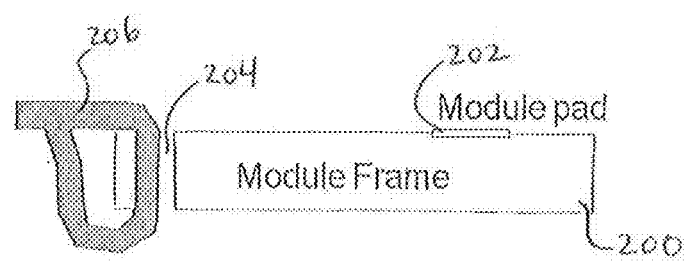
FIG. 8 is a side view of the alumina module frame along line 8-8 of FIG. 7.

Referring now to FIGS. 7-10, a series of figures depicting the steps for attaching a lead wire to an alumina module frame 200 in accordance with the subject technology is shown. Referring now in particular to FIGS. 7 and 8, a top view and side view along line 8-8 of the alumina module frame 200 in accordance with the subject technology is shown. The alumina module frame 200 includes various components shown but not labeled for brevity and clarity. The alumina module frame 200 may contain any number and arrangement of module pads 202.

Preferably, a laser (not shown) is used to drill through holes 204 in the hermetic module frame 200. There may be a hole 204 provided for each pad 202, one hole 204 may connect to multiple pads 202, or multiple holes 204 may connect to a single pad 202 as would be appreciated by those of ordinary skill in the art based upon the subject disclosure. For simplicity, the following discussion relates to one hole 204 connecting to one pad 204.

Still referring to FIG. 8, once the hole 204 is formed, an electrode wire 206 is fed through the hole 204. The electrode wire 206 is secured in place either by wrapping the wire 206 back onto itself or other means. When the wire 206 is wrapped back onto itself, laser or resistive welding can permanently fix the wire 206 to itself. Preferably, the electrode wire 206 is Platinum.

Figure 9:
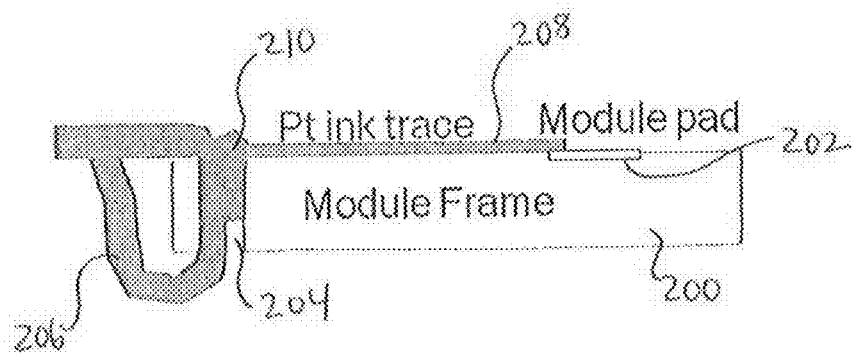
FIG. 9 is a side view of the alumina module frame of FIG. 7 connection between a lead wire and a module pad in accordance with the subject technology.
Figure 10:
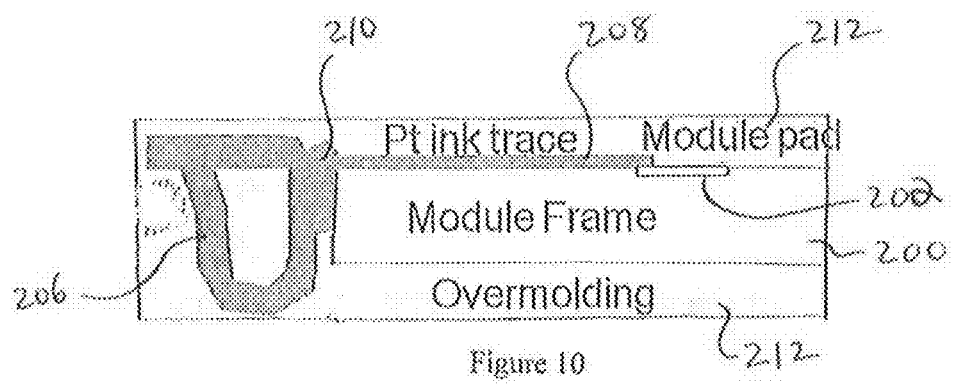
FIG. 10 is a side view of the alumina module frame of FIG. 7 after overmolding in accordance with the subject technology.

Referring now to FIG. 9, another side view of the alumina module frame 200 of FIG. 7 is shown. In order to connect the hermetic module bond pad 202 to the hole 204 and thereby the wire 206, a printed conductive ink trace 208 is applied. Another photo-patterned metal or the like may also be used as the ink trace 208. Typically, the ink trace 208 does not fill the hole 204. Hence, the remainder of the hole 204 is filled with bio-compatible platinum conductive epoxy 210. In one process, the epoxy 210 is applied in a mushroom topology using an ink-jet or aerojet process. Referring now to FIG. 10, a side view of the alumina module frame 200 is shown after overmolding in accordance with the subject technology. Overmolding creates a moisture barrier 212 for protecting the resulting assembly.

As will be appreciated by those of ordinary skill in the pertinent art, the subject technology provides many advantages. For example, it provides a highly reliable electrode connection interface which is bio-compatible. Also, the channel count density (number of pads per $mm^2$ of surface area) can be substantially increased, which allows taking full advantage of miniaturization afforded by integrated ultra-high density (i-UHD) packaging processes. Further, the through-hole lead-wire connection does not rely upon adhesive bonding for shear-strength, enabling long-term electro-mechanical reliability. By using non-conductive adhesives to assure mechanical integrity, the conductive ink can be optimized.

By using the subject technology, reliable, bio-compatible interconnects may achieve a feedthrough density of greater than $2/mm^2$. Assemblies may be stacked with printed conductive via between two bonded modules. The subject technology is application to a wide variety of applications including in the commercial medical community such as in neural stimulation and monitoring, augmentation of hearing and vision, and cardiac assist devices.

FIGS. 11-14 depicts one possible embodiment of the subject technology as a hermetic micropackage 200 interconnected to a high-density electrode array 220 by a high-density interconnect lead wire 230.

Referring now to FIGS. 11-14, another series of figures depicting the steps for forming an electrode array and bonding a hermetic module to the electrode array to form a hermetic micropackage in accordance with the subject technology is shown.

Referring now in particular to FIG. 11, a top view of a semi-conductor wafer 200 with an array of modules 202 is shown. Each module 202 includes a main cavity 204 and a smaller secondary cavity 206. The main cavity 204 will contain the multi-chip module and the secondary cavity 204 will facilitate interconnection to the multi-chip module One or both of the cavities, 204, 206 may be etched as is well known in the art. In another embodiment, the secondary cavity 206 is formed using a laser drill.

Referring additionally to FIG. 12, a perspective view of a single module 202 is shown after completion of readiness for separation from the wafer. As such, the following description is with respect to the single module 202 of FIG. 12 but would apply equally to all modules 202 on the wafer 200. While still integral with the wafer 200, the component 208 is attached in the main cavity 204. Interconnection posts 210 are secured in the secondary cavity 206. A multi-layer thin film interconnection 212 operatively couples the posts 212 to thin film pads 215 of the component 208. The thin film interconnection 212 may be printed or deposited by a lift-off process. A hermetic bather coating 216 is applied to the top of the module 202 (e.g., the component 208) and, preferably, the back of the module 202 as well. At this point, the module 202 can be separated or singulated from the wafer 200.

Figure 14:
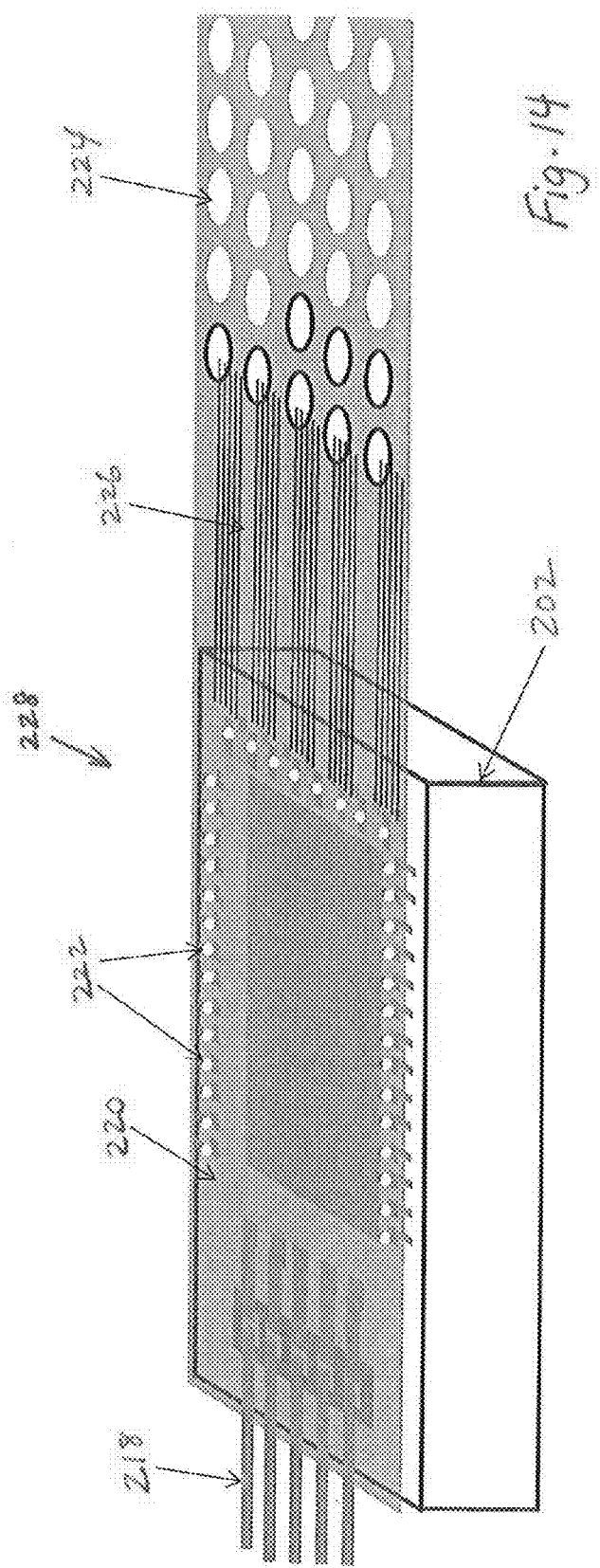
FIG. 14 is a perspective view of a single module post singulation processing connected to an electrode array.

Referring now to FIG. 13, a perspective view of a single module 202 is shown post singulation processing to prepare for connection to an electrode array 224 (see FIG. 14). The post singulation processing includes welding wires or external leads 218 to the posts 210. A flexible electrode 220 is glued to the module 202. The flexible electrode 220 includes a pattern of vias 222 aligned to feedthrough traces 214 not coupled to the interconnection posts 210. The vias 222 may be printed or laser drilled through the flex electrode 220. The printing method described above with respect to FIGS. 1-6 can be utilized to make connections to the feedthrough traces 214.

Referring now to FIG. 14, a perspective view of the single module 202 is shown connected to the electrode array 224. In one embodiment, the electrode array 224 is a high-density flexible electrode array connected to the active circuitry of the component 208 using the printed via connections as described above. High-density interconnect lead wires 226 operatively couple the electrode array 224 to the printed vias 222. The interconnect lead wires 226 and the corresponding traces 214 can be flat metal foil or thin-films. The resulting assembly is a hermetic active micro-package 228. The micro-package 228 can be provided in a sealed enclosed made from a biocompatible material such as titanium.

As would be appreciated, alternate methods may be applied to the subject technology without departing from the innovative concepts and structures. For example, co-fired ceramic feedthroughs involve low densities and high temperature processing. Module thicknesses may be limited to greater than 1 mm thick using hybrid ceramic feedthrough modules.

As would be appreciated by those of ordinary skill in the pertinent art, the functions of several elements as shown may, in alternative embodiments, be carried out by fewer elements, or a single element. Similarly, in some embodiments, any functional element may perform fewer, or different, operations than those described with respect to the illustrated embodiment. Also, functional elements shown as distinct for purposes of illustration may be incorporated within other functional elements, separated in different hardware or distributed in various ways in a particular implementation. Further, relative size and location are merely somewhat schematic and it is understood that not only the same but many other embodiments could have varying depictions.

INCORPORATION BY REFERENCE

All patents, published patent applications and other references disclosed herein are hereby expressly incorporated in their entireties by reference.

While the invention has been described with respect to preferred embodiments, those skilled in the art will readily appreciate that various changes and/or modifications can be made to the invention without departing from the spirit or scope of the invention. For example, each claim may depend from any or all claims, even in a multiple dependent manner, even though such has not been originally claimed.

What is claimed is:

1. A method for bonding a hermetic module to an electrode array comprising:
providing the electrode array having a flexible substrate with a top surface and a bottom surface and including a plurality of pads in the top surface of the substrate;

attaching the hermetic module to the bottom surface of the electrode array, the hermetic module having a plurality of bond-pads, each bond-pad being adjacent to the bottom surface of the electrode array and being configured to align with a corresponding pad;

following the step of attaching, drilling a plurality of holes through each of the plurality of pads to its corresponding bond-pad, wherein each of the pads and its corresponding bond-pad are connected in each of the holes;

filling each drilled hole with biocompatible conductive ink;

forming a rivet on the biocompatible conductive ink over each pad; and overmolding the electrode array with a moisture barrier material.

2. The method of claim 1, wherein the pads are annular.

3. The method of claim 1, further comprising attaching the hermetic module to the electrode array with a bio-compatible non-conductive adhesive.

4. The method of claim 1, further comprising the holes by a laser.

5. The method of claim 1, wherein the holes are substantially circular and less than 50 microns in diameter.

6. The method of claim 1, further comprising using an inkjet or aerojet process to fill each hole with the biocompatible conductive ink.

* * * * *